United States Patent [19]

Neti et al.

[11] 4,077,774

[45] Mar. 7, 1978

[54] INTERFERENT-FREE FLUORESCENCE DETECTION OF SULFUR DIOXIDE

[75] Inventors: Radhakrishna Murty Neti, Brea; Laurence Drell Graham, Claremont, both of Calif.

[73] Assignee: Beckman Instruments, Inc., Fullerton, Calif.

[21] Appl. No.: 768,294

[22] Filed: Feb. 14, 1977

[51] Int. Cl.[2] .............. G01N 21/26; G01N 21/38; G01N 31/12
[52] U.S. Cl. .............................. 23/232 R; 23/254 R
[58] Field of Search ............ 23/232 R, 232 E, 254 R, 23/254 E, 255 R, 255 E

[56] References Cited

U.S. PATENT DOCUMENTS

| 3,567,392 | 3/1971 | Schulze | 23/232 R |
| 3,647,387 | 3/1972 | Benson et al. | 23/232 E X |
| 3,749,929 | 7/1973 | Wooten et al. | 23/232 E X |
| 3,870,468 | 3/1975 | Neti | 23/232 R |
| 3,904,371 | 9/1975 | Neti et al. | 23/232 R |

Primary Examiner—Robert M. Reese
Attorney, Agent, or Firm—Robert J. Steinmeyer; Paul R. Harder; Donald A. Streck

[57] ABSTRACT

Method and apparatus for improved detection of sulfur dioxide by fluorescence are disclosed wherein the effects of interferent hydrocarbons in the test sample are eliminated. In apparatus detecting sulfur dioxide by detecting the fluorescence of sulfur dioxide from narrow band ultraviolet radiation by photomultiplier means, the test sample being fed to the fluorescence chamber is first passed through a reactor to oxidize the hydrocarbons from the sample. The effect of this oxidization is to convert interfering hydrocarbon components in the sample gas into non-interfering materials. In one embodiment employing ozone, moisture removal apparatus is added prior to the oxidization reaction to prevent the error producing formation of $H_2SO_4$.

38 Claims, 2 Drawing Figures

INTERFERENT-FREE FLUORESCENCE DETECTION OF SULFUR DIOXIDE

DESCRIPTION OF THE PRIOR ART

The present invention relates to gas sampling apparatus and more particularly to apparatus detecting and quantizing the amount of sulfur dioxide in a gas sample by fluorescence techniques.

Sulfur dioxide is one of the major air pollutants in the ambient air. As such, it is both desirable and, in many cases, required by law to monitor the quantity of sulfur dioxide contained in the ambient air or contained in a gas stream being exhausted into the ambient air. Currently, sulfur dioxide ($SO_2$) is monitored by any one of several methods such as:

1. The wet chemical coulometric technique, generally known as the West-Gaeke method. 2. Electro-analytical techniques.
3. The $H_2$ flame photometric technique.
4. Gas phase spectrophotometric techniques, including ultraviolet (U.V.) and infrared (I.R.) absorption and U.V. fluorescence.

Of these, the West-Gaeke and the electro-analytical methods are slow in response and are not satisfactory for maintenance-free operation over extended time periods. With the flame photometric method the signal output is not linear with $SO_2$ concentration, and there is also response to other sulfur compounds at varying degrees of sensitivity. U.V. and I.R. absorption techniques are not sufficiently sensitive to monitor part per million (ppm) levels. The U.V. fluorescence technique offers the most promise of not suffering from the above drawbacks.

Sulfur dioxide is known to fluoresce upon excitation with appropriate wavelength light in the ultraviolet region of the electromagnetic spectrum. Recently, the use of U.V. fluorescence has been popularized as a means to monitor ambient sulfur dioxide. A typical fluorescence analyzer consists of a narrow band U.V. light source centered at about 225 nm with about a 25 nm bandwidth, light collimating lenses, a suitable interference filter, a sample fluorescence flow cell, a light trap, a detecting filter, a sensitive photomultiplier tube, a pump, pressure regulating system, and a flow control and/or monitoring system. The operation of this apparatus will be developed later in relation to the description of the preferred embodiment of the present invention. The basic principle of operation is such that the sample gas to be analyzed passes into the fluorescence flow cell, is irradiated by ultraviolet light comprising the above described narrow band of wavelengths selected to be substantially only those wavelengths which will cause $SO_2$ to fluoresce, and the resultant fluorescence of the $SO_2$ contained in the sample is detected and quantized by a photomultiplier tube and associated electronics. Xenon, zinc, and cadmium lamps have been used as light sources to isolate desired wavelengths. The more desirable wavelengths were obtained from the zinc lamp. Instruments so designed by researchers, and at least one commercial producer, apparently operate satisfactorily when tested on certain synthetic gas blends and are claimed to have worked on ambient air. Investigations conducted by the present applicants on such apparatus, however, revealed serious interferences from other gases. When tested individually, some fifteen or so gases (including $NO_x$, CO, and several hydrocarbons) did not show any serious effect on the output data in the detection of $SO_2$ by the U.V. fluorescence method. However, when ambient air with its multiplicity of potential interferents was monitored simultaneously with an $SO_2$ fluorescence analyzer and a coulometric $SO_2$ analyzer (well established for its accuracy) the fluorescence analyzer yielded data vastly different from the coulometric analyzer. Thus, despite claims to the contrary, the fluorescence technique of $SO_2$ monitoring requires improvements beyond the current published state of the art to be of practical value for monitoring of ambient $SO_2$.

Therefore, it is the object of the present invention to provide an improvement in $SO_2$ detection apparatus employed ultraviolet excitation and detection of the emitted fluorescence to overcome the interference drawbacks described above and thus make it possible to obtain reliable measurements.

SUMMARY

The above objective is accomplished by incorporating a reactor in the sample stream ahead of the fluorescence detection apparatus. In one embodiment employing ozone in the reactor, a dryer is added ahead of the reactor. The dryer removes moisture from the incoming sample stream in order to prevent the undesired error producing formation of $H_2SO_4$ in the subsequent reactor. The reactor employs an oxidizer such as heated pure carbon, heated quartz, or the like, or, alternatively, a broad band U.V. light source capable of producing ozone from oxygen within the sample stream. The reactor in each case has an oxidizing effect on the molecules of the interferents whereby the interferents are converted into nonfluorescent materials.

DESCRIPTION OF THE PREFERRED EMBODIMENT

Figure 1:
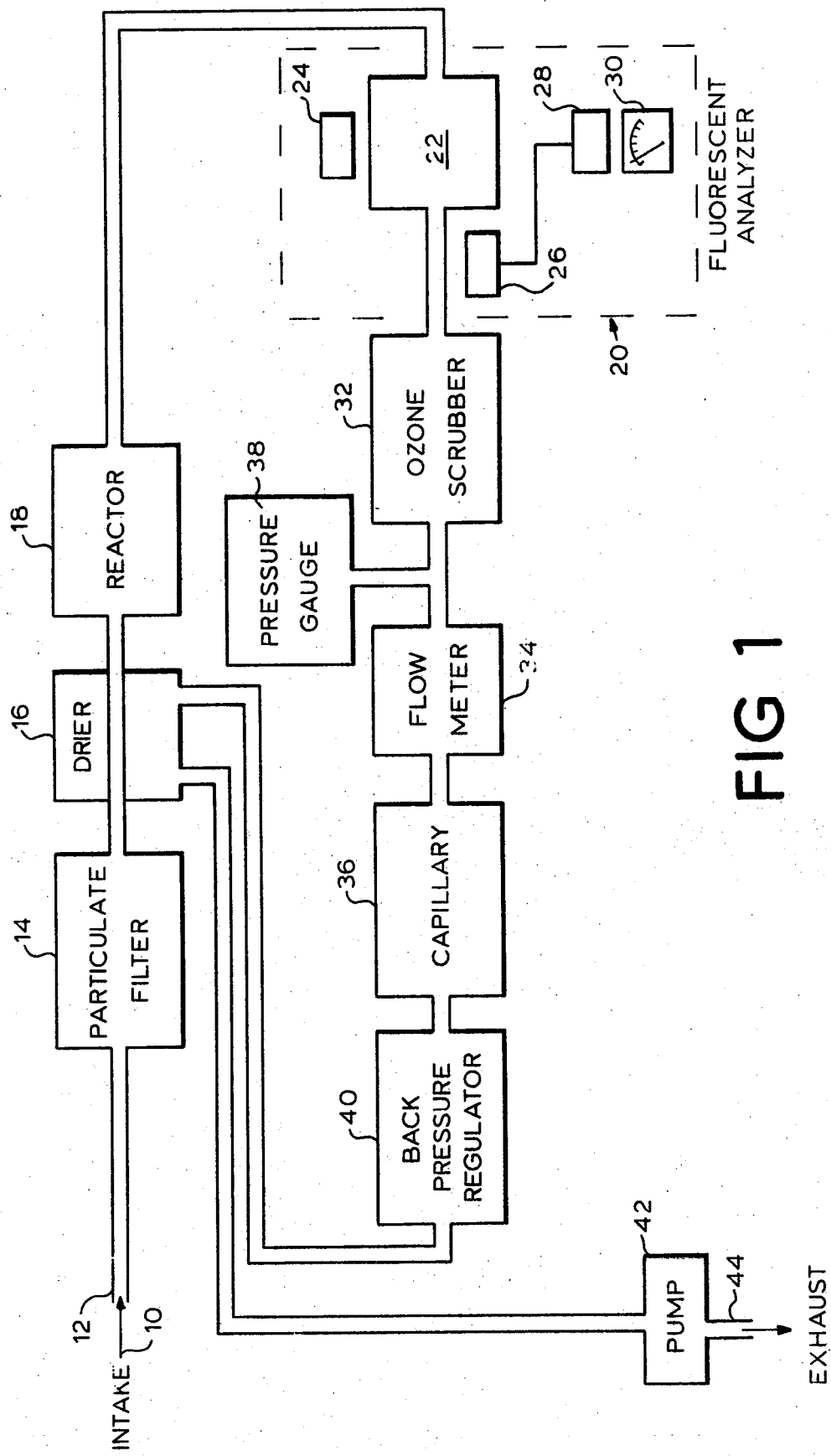
FIG. 1 is a block diagram of the components comprising one embodiment of the improved interferent-free fluorescence detection system for sulfur dioxide of the present invention.

During the development efforts on a fluorescence analyzer for $SO_2$, in order to determine the accuracy and precision of the results being obtained with the prototype fluorescence analyzer, the samples were supplied simultaneously (from the same manifold) to a coulometric analyzer — in particular, a Beckman Model 906 A $SO_2$ Analyzer. The two instruments were exposed to clean calibration samples (both wet and dry) obtained either by passing clean air over an $SO_2$ permeation tube or by taking a compressed mixture of $SO_2$ and clean air directly from a steel cylinder. The coulometric analyzer, being a primary instrument, required no span adjustment, and its reading was taken as the standard. The fluorescence analyzer was adjusted accordingly. Once calibrated at one value (approximately 1 ppm) the two analyzers tracked within ±1% over a concentration range between 5 ppb and 2,000 ppb (2 ppm).

When the two analyzers were exposed to ambient samples, however, the responses diverged over a wide range. With ambient $SO_2$, typically in the range of 5–50 ppb, as measured by the coulometric analyzer, the fluorescence analyzer would show a response anywhere from that indicated by the coulometric analyzer (never lower) up to as much as 250 ppb (under the worst conditions) depending upon the prevailing ambient composition of minor pollutants. The ambient air contained varying amounts of ozone, oxides of nitrogen, and many hydrocarbons. Conditions were also found to fluctuate as of the time of day. The "worst" ambient conditions occurred typically from 8-10 a.m. and 4-6 p.m. Because of the time of day of these "worst" conditions and the environment associated with them, the prime interferents were postulated as being hydrocarbons; in particular, polynuclear aromatic hydrocarbons. Interfering components are believed to include acenaphthene, acenaphthylene, anthracene, benz[a]anthracene-7,12-dione, benzo[ghi]perylene, crysene, coronene, dibenzofuran, dibenzothiophene, fluoranthrene, naphthalene, perylene, phenanthrene, and pyrene.

One of the co-inventors of the present invention was also the co-inventor of a reactor capable of removing hydrocarbons as interferents in a sample gas stream. This reactor is described in the co-pending U.S. patent application 704,268 by R. M. Neti and R. L. Roggenkamp which is assigned to the common assignee of the present application. The feasibility of employing that reactor with a fluorescence $SO_2$ analyzer was, therefore, investigated. In order to make the fluorescence analyzer response using the samples as described above agree ($\pm 5$ ppb, or less on a range of 250 ppb full scale) with that of the coulometric analyzer the sample (through the fluorescence analyzer only) was conditioned by passing it through a reactor comprising an enclosure containing a high purity quartz lamp producing ultraviolet light at the 184.9, 253.7, 303.6 and 403.6 nm bands. The action of this broad band U.V. light and, possibly, synergistically the ozone produced by the lamp from the oxygen in the passing air, was to oxidize the interferent, and agreement as specified above between response of the fluorescence and coulometric analyzers was obtained.

The above described agreement, however, between the responses of the fluorescence analyzer with the sample gas passing through the U.V. oxidizing reactor and the coulometric analyzer was found to hold only for dry samples, both ambient and synthetic. Whereas water vapor had not been an interferent before the U.V. radiation was introduced, a strong quenching of the $SO_2$ response by water vapor was found in the fluorescence analyzer after the U.V. irradiation containing 184.9 nm line was added. The fluorescence analyzer response showed an attenuation of up to the order of 90% while the coulometric analyzer showed at most a 10% loss of output when water vapor was added to samples containing $SO_2$. These experiments suggested that in the U.V. irradiation process within the enclosure, in the presence of water vapor, $SO_2$ was being oxidized to $SO_3$ and, presumably, to $H_2SO_4$, resulting in loss of signal from the conditioned sample. This quenching due to the presence of water vapor in the U.V. conditioned samples was, obviously, undesirable. The quenching was eliminated by drying the sample by passing it through a high quality, commercially available dryer prior to passing it through the U.V. reactor. The dryer selected had to be capable of removing the water vapor interferents without attenuating the $SO_2$ response. A dryer employing a technique called Permeation Distillation as manufactured by Perma Pure Products, Inc. of Oceanport, N.J. was found to work well for the application. With the combined arrangement wherein the sample gas is first dried by a dryer and then U.V. irradiated by exposure to the quartz lamp, ambient samples monitored simultaneously on the coulometric analyzer and on the fluorescence analyzer had responses agreeing to within $\pm 5$ ppb $SO_2$, or better, on the range of 250 ppb full scale. These results were found to be true for all possible "reasonable" ambient conditions that were investigated. As an example of "unreasonable" conditions, when the intake for the fluorescence analyzer was placed, literally, in the plume of an automobile exhaust, facing into the plume, and within two feet of the exhaust pipe, the interferences, although very dramatically reduced, could not be entirely removed by the dryer and quartz lamp U.V. irradiation combination.

Apparatus for practicing the present invention in its first developed embodiment is shown in FIG. 1. The sample gas 10 is introduced at intake 12. From intake 12 the sample gas passes through a particulate filter 14 which removes particulate matter from the sample gas 10. Sample gas 10 then passes through a dryer 16 connected to the particulate filter 14. Ideally, dryer 16 should be capable of removing substantially all of the moisture from sample gas 10 while not affecting the $SO_2$ content thereof. The Permeation Distillation type dryer described above is presently preferred in this embodiment. The output of dryer 16 is connected to a U.V. reactor 18 capable of removing the effect of the interferents in the sample gas 10 by an oxidation process. It is preferred that reactor 18 comprise an enclosure containing a high purity quartz lamp emitting a broad band of wavelengths, including 1849 nm line (which will cause the generation of ozone from oxygen in the sample gas 10) and 253.7 nm line, of U.V. light disposed to irradiate a gas sample passing therethrough. The output of the oxidizing reactor 18 is connected to the input of a fluorescence analyzer generally indicated as 20. Fluorescence analyzer 20 comprises a fluorescence chamber 22 into which the sample gas 10 passes. A source of ultraviolet illumination 24 is positioned to direct narrow band, collimated ultraviolet light centered at about 225.0 nm into fluorescence chamber 22 where it strikes the sample gas 10 causing any $SO_2$ contained therein to fluoresce. The fluorescence of the $SO_2$ within sample gas 10 in fluorescence chamber 22 is detected by photomultiplier means 26 which is connected through appropriate electronic circuitry 28 to display means 30 which indicates the $SO_2$ content of the sample gas 10 in a form understandable by an operator. The output of fluorescence analyzer 20 is connected to an ozone scrubber 32 which removes any ozone produced by the reactor 20 from oxygen in the sample gas 10 and remaining in the sample stream. The ozone should be removed to prevent damage to parts within the back pressure regulator and pump contained in the downstream portion of the apparatus. A flowmeter 34 is connected to the output of ozone scrubber 32 and a capillary 36 is, in turn, connected to the output of the flowmeter 34. A pressure gauge 38 is connected into the connection between ozone scrubber 32 and flowmeter 34. The system between the intake 12 and capillary 36, therefore, is intended to operate at atmospheric pressure and constant flow so that the indicated detection of $SO_2$ is independent of pressure. Pressure gauge 38 permits monitoring of the pressure within chamber 22 which could change as, for example, by clogging of particulate filter 14. A back pressure regulator 40 for maintaining the flow rate steady is connected to the output of capillary 36. Back pressure regulator 40, in turn, is connected to the inlet of the "bootstrap" portion of dryer 16 which uses the dried sample at a reduced pressure to aid in the drying process in a manner characteristic of the Permeation Distillation dryers employing semi-permeable membrane which were found to work particularly well in this application. The outlet of the "bootstrap" portion of dryer 16 is connected to a pump 42 used to create a partial vacuum to draw the sample gas 10 through fluorescence analyzer 20 and also aid in the drying process. The output of pump 42 is connected to exhaust outlet 44.

Flow rates through the system are not critical. Approximately 1000–1500 cc/min has been found to work well and is preferred. If the flow rate is too fast, the interferents will not have time to be completely removed by the reactor.

While the method and apparatus described to this point work well for the intended purpose, the necessity of employing a drier and an ozone scrubber adds a negative factor to the commercial marketability of such an instrument because of the added costs. An alternate embodiment which could oxidize the interferents without the need for the drier and ozone scrubber was, therefore, sought. In pursuit of such a viable alternate embodiment, various reactors used in the present assignee's instruments were investigated as to their adaptability for use as a hydrocarbon oxidizer in a sample gas stream containing $SO_2$. One such reactor is described in U.S. Pat. No. 3,870,468 to R. M. Neti (also assigned to the common assignee of this application) for Nitrogen Dioxide Analysis. The patent discloses converting nitrogen dioxide to nitric oxide for subsequent detection by chemiluminescence techniques by passing the nitrogen dioxide through a reactor comprising a confined volume wherein concentrated heat is applied to the volume in the presence of vitreous carbon (also known as glassy carbon). When a sample gas containing the interferent hydrocarbons was passed through such a reactor, it was found that the hydrocarbons were virtually completely oxidized while the $SO_2$ contained therein was virtually unaffected. While other means of oxidizing the hydrocarbons in the sample stream without adverse effect on the $SO_2$ content were found, the vitreous carbon reactor has become the preferred embodiment as of the time of filing the present application.

While a more detailed description of several embodiments of a vitreous carbon reaction are contained in the above referenced Pat. No. 3,870,468, the construction can be stated quite simply. The reactor comprises a confined path through which the sample gas is passed. Within the confined path is contained a virtually impurity-free carbon heated to from 300° to 600° C with about 450° C being preferred. Satisfactory carbons employed in tested embodiments have been obtained from POCO Graphite, Inc. of Garland, Texas and Beckwith, Corp. of Van Nuys, California. The former refers to their product as POCO graphite and the latter refers to theirs as vitreous carbon. In its description of nitrogen dioxide conversion, the patent suggests vitreous carbon pellets or rods. Superior results were obtained in the present application using POCO graphite X4029 (fine pellets) which transmits $SO_2$ without any hesitation.

While not specifically tested, prior experience leads to the conclusion that softer forms of high-purity carbon would be used at substantially lower temperatures. Such reactors, of course, would have to be recharged from time to time (as opposed to the harder vitreous carbon reactors) as the carbon is consumed. Experience also dictates the avoidance of so-called "activated" carbon as it would tend to trap and extract the $SO_2$ as well.

Figure 2:
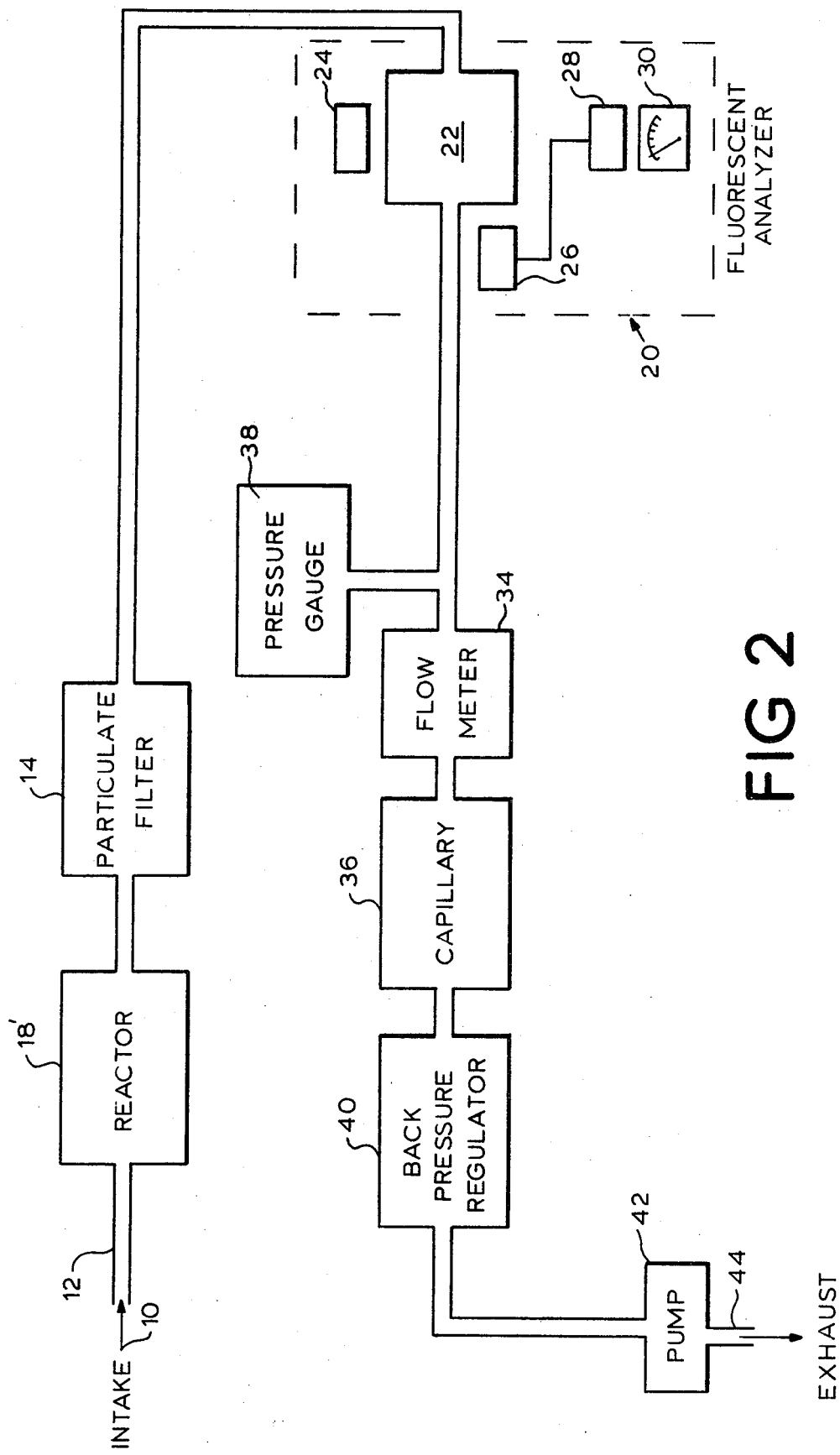
FIG. 2 is a block diagram of the components comprising the preferred embodiment of the improved interferent-free fluorescence detection system for sulfur dioxide of the present invention.

Apparatus for practicing the present invention in its preferred embodiment is shown in FIG. 2. Corresponding elements are designated as in FIG. 1 and have identical functions. As desired, dryer 16 and ozone scrubber 32 are no longer necessary and are, consequently, eliminated. Vitreous carbon reactor 18'0 has replaced U.V. reactor 18 but continues the identical function of providing means for oxidizing the hydrocarbons in sample gas 10. While reactor 18' is repositioned ahead of particulate filter 14, this is a matter of choice only as the particulate filter 14 is an optional feature (as are pressure gauge 38 and flowmeter 34) included as preferred to give superior performance in commercially marketed instruments.

While U.V. with ozone and ultra-high-purity carbon in the presence of heat have heretofore been described in great detail as acceptable and preferred (respectively) means for oxidizing hydrocarbons in a gas sample stream without affecting the $SO_2$ content thereof, additional means were considered and, in many cases, tested. A number have sufficient promise to be considered as viable alternatives for direct substitution as hydrocarbon oxidizing reactor 18' in the $SO_2$ detection system of FIG. 2. These include quartz heated to greater than 700° C, with quartz at 900° C giving the best results; and stainless steel heated to about 400° C. In some cases, however, there was some loss of $SO_2$ when employing the hot stainless steel.

Additionally, platinum black or palladium maintained between ambient and 200° C were able to oxidize the hydrocarbons, but were moisture sensitive. To employ either, therefore, would require the including of a dryer as in FIG. 1, but no ozone scrubber.

Having thus described our invention, we claim:

1. The improved method of detecting sulfur dioxide in a gas sample comprising the steps of:
   (a) passing the gas sample through a reactor which oxidizes hydrocarbons and passes sulfur dioxide;
   (b) irradiating the gas sample with ultraviolet light; and,
   (c) measuring the level of fluorescence of the gas sample in response to said irradiation whereby the quantity of sulfur dioxide in the gas sample is determined.

2. The method of claim 1 wherein: the reactor contains stainless steel heated to about 400° C.

3. The method of claim 1 wherein:
   (a) the gas sample is dried to remove moisture contained therein prior to the step of passing the gas sample through a reactor; and
   (b) the reactor contains a material selected from the group consisting of platinum black and palladium maintained at between ambient temperature and 200° C.

4. The method of claim 1 wherein:
   (a) the gas sample is dried to remove moisture contained therein prior to the step of passing the gas sample through a reactor;
   (b) the reactor irradiates the gas sample with broad band ultraviolet light; and,
   (c) the irradiation step (b) of claim 1 is accomplished with narrow band ultraviolet light.

5. The method of claim 4 wherein:

the broad band ultraviolet irradiation of the gas sample in the reactor takes place in the presence of oxygen.

6. The method of claim 1 wherein:
the reactor contains quartz heated to greater than 700° C.

7. The method of claim 6 wherein:
the quartz is maintained at about 900° C.

8. The method of claim 1 wherein:
the reactor contains high purity carbon.

9. The method of claim 8 wherein:
the high purity carbon is vitreous carbon heated to the range of from 300° to 600° C.

10. The method of claim 9 wherein:
the high purity carbon is maintained at about 450° C.

11. Improved apparatus for detecting sulfur dioxide in a gas sample comprising:
(a) a reactor for conditioning any interferents in the gas sample to eliminate fluorescence thereof during the subsequent analysis of the gas sample, said reactor having an input for receiving the gas sample and an output;
(b) a fluorescence chamber connected to said output of said reactor and adapted to hold the gas sample;
(c) a source of narrow band ultraviolet light disposed to irradiate the gas sample in said chamber; and,
(d) photomultiplier means disposed to measure the level of fluorescence of the gas sample when being irradiated by said narrow band ultraviolet light and including means for displaying said measured level of fluorescence as a measure of the quantity of sulfur dioxide in the gas sample.

12. The apparatus of claim 11 wherein said reactor includes:
(a) stainless steel; and,
(b) means for heating said stainless steel to about 400° C.

13. The apparatus of claim 11 wherein said reactor includes:
(a) high purity carbon; and,
(b) means for heating said carbon to the range of from 300° to 600° C.

14. The apparatus of claim 13 wherein:
said heating means is adapted to maintain said carbon at about 450° C.

15. The apparatus of claim 11 wherein said reactor includes:
(a) quartz; and,
(b) means for heating said quartz to greater than 700° C.

16. The apparatus of claim 15 wherein:
said heating means is adapted to maintain said quartz at about 900° C.

17. The apparatus of claim 11 and additionally comprising:
a dryer having an input and an output, said dryer being adapted to remove moisture from a gas passing therethrough while not affecting any sulfur dioxide contained in said gas, said input being adapted to receive the gas sample, said output being connected to the input of said reactor.

18. The apparatus of claim 17 wherein said reactor includes:
a source of ultraviolet light containing wavelengths at the 184.9 and 253.7 nm bands whereby fluorescence of any interferents under narrow band ultraviolet irradiation capable of causing SO₂ to fluoresce is eliminated.

19. The apparatus of claim 17 wherein said reactor includes:
a source of ultraviolet light containing wavelengths capable of producing ozone from oxygen in the gas sample.

20. The apparatus of claim 17 wherein said reactor includes:
(a) a material selected from the group consisting of platinum black and palladium; and,
(b) means for heating said material from ambient temperature to about 200° C.

21. Improved apparatus for detecting sulfur dioxide in a gas sample comprising:
(a) a reactor for oxidizing any hydrocarbons in the gas sample to eliminate error producing reaction thereof during the subsequent analysis of the gas sample, said reactor having an input for receiving the gas sample and an output;
(b) a fluorescence chamber connected to said output of said reactor and adapted to hold the gas sample;
(c) a source of narrow band ultraviolet light disposed to irradiate the gas sample in said chamber; and,
(d) photomultiplier means disposed to measure the level of fluorescence of the gas sample when being irradiated by said narrow band ultraviolet light and including means for displaying said measured level of fluorescence as a measure of the quantity of sulfur dioxide in the gas sample.

22. The apparatus of claim 21 wherein said reactor includes:
(a) stainless steel; and,
(b) means for heating said stainless steel to about 400° C.

23. The apparatus of claim 21 wherein said reactor includes:
(a) high purity carbon; and,
(b) means for heating said carbon to the range of from 300° to 600° C.

24. The apparatus of claim 23 wherein:
said heating means is adapted to maintain said carbon at about 450° C.

25. The apparatus of claim 21 wherein said reactor includes:
(a) quartz; and,
(b) means for heating said quartz to greater than 700° C.

26. The apparatus of claim 25 wherein:
said heating means is adapted to maintain said quartz at about 900° C.

27. The apparatus of claim 21 and additionally comprising:
a dryer having an input and an output, said dryer being adapted to remove moisture from a gas passing therethrough while not affecting any sulfur dioxide contained in said gas, said input being adapted to receive the gas sample, said output being connected to the input of said reactor.

28. The apparatus of claim 27 wherein said reactor includes:
a source of ultraviolet light containing wavelengths at the 184.9 and 253.7 nm bands whereby fluorescence of any interferents under narrow band ultraviolet irradiation capable of causing SO₂ to fluoresce is eliminated.

29. The apparatus of claim 27 wherein said reactor includes:

a source of ultraviolet light containing wavelengths capable of producing ozone from oxygen in the gas sample.

30. The apparatus of claim 27 wherein said reactor includes:
   (a) a material selected from the group consisting of platinum black and palladium; and,
   (b) means for heating said material from ambient temperature to about 200° C.

31. Apparatus for removing the effect of interferents from a gas sample to be analyzed for sulfur dioxide content by a fluorescence analyzer comprising:
   (a) a dryer having an input and an output, said dryer being adapted to remove moisture from a gas passing therethrough while not affecting any sulfur dioxide contained in said gas, said input being adapted to receive the gas sample; and,
   (b) a reactor for conditioning the interferents to eliminate fluorescence thereof during the subsequent analysis of the gas sample, said reactor having an input connected to said output of said dryer and an output adapted to be connected to the input of the fluorescence analyzer.

32. The apparatus of claim 31 wherein said reactor includes:
   a source of ultraviolet light containing wavelengths at the 184.9 and 253.7 nm bands whereby fluorescence of the interferents under narrow band ultraviolet irradiation capable of causing $SO_2$ to fluoresce is eliminated.

33. The apparatus of claim 31 wherein said reactor includes:
   a source of ultraviolet light containing wavelengths capable of producing ozone from oxygen in the gas sample.

34. The apparatus of claim 31 wherein said reactor includes:
   (a) a material selected from the group consisting of platinum black and palladium; and,
   (b) means for heating said material from ambient temperature to about 200° C.

35. Apparatus for removing the effect of interferent hydrocarbons from a gas sample to be analyzed for sulfur dioxide content by a fluorescence analyzer comprising:
   (a) a dryer having an input and an output, said dryer being adapted to remove moisture from a gas passing therethrough while not affecting any sulfur dioxide contained in said gas, said input being adaped to receive the gas sample; and,
   (b) a reactor for oxidizing the hydrocarbons to eliminate error producing reaction thereof during the subsequent analysis of the gas sample while passing the sulfur dioxide unaffected, said reactor having an input connected to said output of said dryer and an output adapted to be connected to the input of the fluorescence analyzer.

36. The apparatus of claim 35 wherein said reactor includes:
   a source of ultraviolet light containing wavelengths at the 184.9 and 253.7 nm bands whereby fluorescence of the interferents under narrow band ultraviolet irradiation capable of causing $SO_2$ to fluoresce is eliminated.

37. The apparatus of claim 35 wherein said reactor includes:
   a source of ultraviolet light containing wavelengths capable of producing ozone from oxygen in the gas sample.

38. The apparatus of claim 35 wherein said reactor includes:
   (a) a material selected from the group consisting of platinum black and palladium; and,
   (b) means for heating said material from ambient temperature to about 200° C.

* * * * *